(12) United States Patent
Qi et al.

(10) Patent No.: US 7,419,982 B2
(45) Date of Patent: Sep. 2, 2008

(54) CRYSTALLINE FORMS OF 5-CHLORO-6-{2,6-DIFLUORO-4-[3-(METHYLAMINO)PROPOXY]PHENYL}-N-[(1S)-2,2,2-TRIFLUORO-1-METHYLETHYL][1,2,4]TRIAZOLO[1,5-A]PYRIMIDIN-7-AMINE SALTS

(75) Inventors: Fang Fang Qi, New City, NY (US); Mannching Sherry Ku, Thiells, NY (US); Yanzhong Wu, Bardonia, NY (US); David M. Blum, Upper Saddle River, NJ (US)

(73) Assignee: Wyeth Holdings Corporation, Madison, NJ (US)

( * ) Notice: Subject to any disclaimer, the term of this patent is extended or adjusted under 35 U.S.C. 154(b) by 0 days.

(21) Appl. No.: 11/437,291

(22) Filed: May 19, 2006

(65) Prior Publication Data
US 2007/0060597 A1   Mar. 15, 2007

Related U.S. Application Data

(63) Continuation-in-part of application No. 10/950,543, filed on Sep. 24, 2004.

(60) Provisional application No. 60/505,544, filed on Sep. 24, 2003.

(51) Int. Cl.
  *A01N 43/90* (2006.01)
  *A61K 31/519* (2006.01)
  *C07D 487/00* (2006.01)
(52) U.S. Cl. .................. 514/259.31; 544/263
(58) Field of Classification Search ........... None
   See application file for complete search history.

(56) References Cited

U.S. PATENT DOCUMENTS

| | | | |
|---|---|---|---|
| 5,593,996 | A | 1/1997 | Pees et al. |
| 5,612,345 | A | 3/1997 | Becher et al. |
| 5,750,766 | A | 5/1998 | Krummel et al. |
| 5,756,509 | A | 5/1998 | Pees et al. |
| 5,808,066 | A | 9/1998 | Krummel et al. |
| 5,817,663 | A | 10/1998 | Pees et al. |
| 5,854,252 | A | 12/1998 | Pees et al. |
| 5,948,783 | A | 9/1999 | Pees et al. |
| 5,955,252 | A | 9/1999 | Goto et al. |
| 5,965,561 | A | 10/1999 | Pees et al. |

(Continued)

FOREIGN PATENT DOCUMENTS

EP   0 550 113   7/1993

(Continued)

OTHER PUBLICATIONS

Berge et. al., J. Pharm. Sci. 1997, 66(1), p. 1-19.*

(Continued)

*Primary Examiner*—James O Wilson
*Assistant Examiner*—Jeffrey H Murray
(74) *Attorney, Agent, or Firm*—Wilmer Cutler Pickering Hale and Dorr LLP

(57) ABSTRACT

The present invention relates to crystalline forms of 5-chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine salts; processes for the production thereof; pharmaceutical compositions thereof; and methods for inhibiting tumor growth therewith.

15 Claims, 8 Drawing Sheets

U.S. PATENT DOCUMENTS

| | | | |
|---|---|---|---|
| 5,981,534 | A | 11/1999 | Pfrengle et al. |
| 5,985,883 | A | 11/1999 | Pees et al. |
| 5,986,135 | A | 11/1999 | Pfrengle et al. |
| 5,994,360 | A | 11/1999 | Pfrengle et al. |
| 6,020,338 | A | 2/2000 | Pfrengle et al. |
| 6,117,865 | A | 9/2000 | Pees et al. |
| 6,117,876 | A | 9/2000 | Pees et al. |
| 6,124,301 | A | 9/2000 | Aven et al. |
| 6,204,269 | B1 | 3/2001 | Pfrengle et al. |
| 6,242,451 | B1 | 6/2001 | Pees et al. |
| 6,255,309 | B1 | 7/2001 | Pees et al. |
| 6,268,371 | B1 | 7/2001 | Sieverding et al. |
| 6,277,856 | B1 | 8/2001 | Cotter et al. |
| 6,284,762 | B1 | 9/2001 | Pfrengle et al. |
| 6,297,251 | B1 | 10/2001 | Pees et al. |
| 6,387,848 | B1 | 5/2002 | Aven et al. |
| 6,518,275 | B1 | 2/2003 | Van Tuyl Cotter et al. |
| 6,521,628 | B1 | 2/2003 | Cotter et al. |
| 6,699,874 | B2 | 3/2004 | Cotter et al. |
| 2002/0045631 | A1 | 4/2002 | Aven et al. |
| 2002/0061882 | A1 | 5/2002 | Pees et al. |
| 2002/0068744 | A1 | 6/2002 | Schmitt et al. |
| 2002/0198222 | A1 | 12/2002 | Bruns et al. |
| 2003/0055069 | A1 | 3/2003 | Pees et al. |
| 2004/0097522 | A1 | 5/2004 | Gebauer et al. |
| 2005/0030775 | A1 | 2/2005 | Lipcsei |
| 2005/0090508 | A1* | 4/2005 | Zhang et al. ........... 514/259.31 |
| 2005/0124635 | A1* | 6/2005 | Wu et al. ............... 514/259.31 |

FOREIGN PATENT DOCUMENTS

| | | |
|---|---|---|
| EP | 0 562 615 | 9/1993 |
| EP | 0 782 997 | 7/1997 |
| EP | 0 834 513 | 4/1998 |
| EP | 0 943 241 | 9/1999 |
| EP | 0 945 453 | 9/1999 |
| EP | 0 988 790 | 3/2000 |
| EP | 0 989 130 | 3/2000 |
| FR | 2 784 381 | 4/2000 |
| WO | WO-94/20501 | 9/1994 |
| WO | WO-98/41496 | 9/1998 |
| WO | WO-98/46607 | 10/1998 |
| WO | WO-99/41255 | 8/1999 |
| WO | WO-99/48893 | 9/1999 |
| WO | WO-00/18227 | 4/2000 |
| WO | WO-01/35738 | 5/2001 |
| WO | WO-02/02563 | 1/2002 |
| WO | WO-02/38565 | 5/2002 |
| WO | WO-02/46195 | 6/2002 |
| WO | WO-02/50077 | 6/2002 |
| WO | WO-02/067679 | 9/2002 |
| WO | WO-02/083676 | 10/2002 |
| WO | WO-03/008416 | 1/2003 |

OTHER PUBLICATIONS

Brittain et. al., 1999, "Effects of Pharmaceutical Processing on drug polymoprhys and solvates."In Polymorphism in Pharmaceutical Solids, pp. 331-361.*
http://www.expresspharmaonline.com/20031012/edit02.shtml (3 pages) Jul. 2007.*
Byrn et al., "Solid State analysis of the active pharmaceutical ingredient in drug products", 2003, DDT, vol. 8, No. 19, 898-905.*
Bicher, et al., Anti-Cancer Drugs, 4:141-148 (1993).
Brill, J. Am. Chem. Soc., 54:2484-2487 (1932).
Chini, et al., Tetr. Lett., 35(5): 761-764 (1994).
Goldstein, et al., J. Natl. Cancer Inst., 81:116-124 (1989).
Gottesman, Ann. Rev. Med., 53:615-627 (2002).
Gottesman, et al., Nature Rev. Cancer, 2:48-58 (2002).
Hamel, et al., J. Biol. Chem., 259(4):2501-2508 (1984).
Hamel, Med. Res. Rev., 16:207-231 (1996).
Holmes, et al., J. Natl. Cancer Inst., 83(24):1797-1805 (1991).
Holton, et al., J. Am. Chem. Soc., 116(4):1597-1600 (1994).
Jones, et al., J. Chem. Soc. (B), pp. 1300-1315 (1971).
Jordan, et al., Cancer Res., 56:816-825 (1996).
Koepke, et al., J. Org. Chem., 44(15):2718-2722 (1979).
Kohn, et al., Natl. Cancer Inst., 86(1):18-24 (1994).
Kumar, J. Biol. Chem., 256(20):10435-10441 (1981).
Li, et al., Science & Medicine, Jan./Feb., pp. 38-47 (1999).
Loganzo, et al., Cancer Res. 63:1838-1845 (2003).
McGrath, et al., Biochem. Biophys. Res. Commun., 145(3):1171-1176 (1987).
McGuire, et al., Ann. Int. Med., 111(4):273-279 (1989).
Monteil, et al., J. Organomet Chem, 480:177-184 (1994).
Nicolaou, et al., Nature, 367:630-634 (1994).
Oka, et al., Tetrahedron, 54:1-20 (1998).
Rabindran, et al., Cancer Res., 58:5850-5858 (1998).
Rowinsky, et al., "Antimicrotubule Agents", *Cancer: Principles and Practice of Oncology*, Chapter 19, Section 7, pp. 431-452 (2001).
Rowinsky, et al., Natl. Cancer Inst., 82(15):1247-1259 (1990).
Schiff, et al., Nature, 277-665-667 (1979).
Shen, et al., J. Boil. Chem., 261(17):7762-7770 (1986).
Wani, et al., J. Am. Chem. Soc., 93:2325-2327 (1971).
International Search Report and Written Opinion issued in PCT/US2007/011817, dated Dec. 13, 2007.

* cited by examiner

Experimental PXRD pattern for 5-chloro-6-{2,6-difluoro-4-[3-(methylamino)propoxy]
phenyl}-N-[(1S)-2,2,2-trifluoro-1-methylethyl][1,2,4]triazolo[1,5-a]pyrimidin-7-amine
succinate dihydrate DSC Thermogram for 5-chloro-6-{2,6-difluoro-4-[3-(methylamino)propoxy]phenyl}-N-(1S)-2,2,2-trifluoro-1-methylethyl][1,2,4]triazolo[1,5-a]pyrimidin-7-amine succinate dehydrate Temp (° C)

TGA Thermogram for 5-chloro-6-{2,6-difluoro-4-[3-(methylamino)propoxy]phenyl}-N-
[(1S)-2,2,2-trifluoro-1-methylethyl][1,2,4]triazolo[1,5-a]pyrimidin-7-amine succinate
dihydrate Temp (° C)

Experimental PXRD pattern for 5-chloro-6-{2,6-difluoro-4-[3-(methylamino)propoxy]
phenyl}-N-[(1S)-2,2,2-trifluoro-1-methylethyl][1,2,4]triazolo[1,5-a]pyrimidin-7-amine
succinate anhydrous Experimental PXRD pattern for 5-chloro-6-{2,6-difluoro-4-[3-(methylamino)propoxy]
phenyl}-N-[(1S)-2,2,2-trifluoro-1-methylethyl][1,2,4]triazolo[1,5-a]pyrimidin-7-amine
fumarate dihydrate DSC Thermogram for 5-chloro-6-{2,6-difluoro-4-[3-(methylamino)propoxy] phenyl}-N-[(1S)-2,2,2-trifluoro-1-methylethyl][1,2,4]triazolo[1,5-a]pyrimidin-7-amine fumarate dihydrate Temp (° C)

Experimental PXRD pattern for 5-chloro-6-{2,6-difluoro-4-[3-(methylamino)propoxy]
phenyl}-N-[(1S)-2,2,2-trifluoro-1-methylethyl][1,2,4]triazolo[1,5-a]pyrimidin-7-amine
mandelate DSC Thermogram for 5-chloro-6-{2,6-difluoro-4-[3-(methylamino)propoxy] phenyl}-N-[(1S)-2,2,2-trifluoro-1-methylethyl][1,2,4]triazolo[1,5-a]pyrimidin-7-amine mandelate dihydrate Temp (° C)

CRYSTALLINE FORMS OF 5-CHLORO-6-{2,6-DIFLUORO-4-[3-(METHYLAMINO)PROPOXY]PHENYL}-N-[(1S)-2,2,2-TRIFLUORO-1-METHYLETHYL][1,2,4]TRIAZOLO[1,5-A]PYRIMIDIN-7-AMINE SALTS

RELATED APPLICATION

This application is a continuation-in-part of application Ser. No. 10/950,543, filed Sep. 24, 2004, which claims priority to Provisional Application No. 60/505,544, filed Sep. 24, 2003.

FIELD OF THE INVENTION

The present invention relates to crystalline forms of 5-chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine salts; processes for the production thereof; pharmaceutical compositions thereof; and methods for inhibiting tumor growth therewith.

BACKGROUND OF THE INVENTION 5-chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine has the following structure:

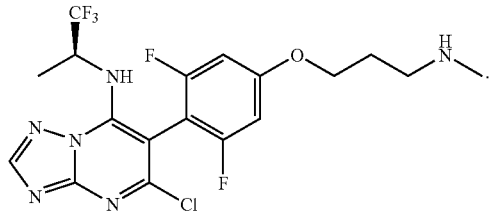

It is a triazolopyrimidine microtubule-active compound which has broad antitumor activity in in-vivo xenograft models of human non-small cell lung cancer (NSCLC), colon cancer, breast cancer, melanoma, and glioblastoma, including models which are resistant to taxanes or other microtubule-active compounds.

This class of triazolopyrimidine compounds is disclosed by Zhang et al. in US 2005/0090508, the disclosure of which is incorporated herein by reference in its entirety. A pharmaceutical formulation of a triazolopyrimidine compound is described in commonly assigned, co-pending patent Application Ser. No. 60/751,131, filed on Dec. 16, 2005, the disclosure of which is incorporated herein by reference in its entirety. The triazolopyrimidine compounds bind at the vinca site of β-tubulin, yet they have many properties that are similar to taxanes and distinct from vinca-site agents. In particular, these compounds enhance the polymerization of microtubule-associated protein (MAP)-rich tubulin in the presence of GTP at low compound:tubulin molar ratios, in a manner similar to paclitaxel and docetaxel. The triazolopyrimidine compounds also induce polymerization of highly purified tubulin in the absence of GTP under suitable experimental conditions, an activity that is a hallmark of taxanes. These compounds are potently cytotoxic for many human cancer cell lines in culture, including lines that overexpress the membrane transporters MDR (P-glycoprotein), MRP, and MXR, thus making them active against cell lines that are resistant to paclitaxel and vincristine. In particular, representative examples of this class of triazolopyrimidine compounds have high water solubility and can be formulated in aqueous solution. Representative examples of the triazolopyrimidine compounds are active as anti-tumor agents in athymic mice bearing human tumor xenografts of lung and colon carcinoma, melanoma, and glioblastoma, when dosed either intravenously or orally.

The physical and chemical properties of 5-chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine that results in challenges to the successful formulations of oral and liquid dosage forms include poor solubility in water and chemical instability due to several mechanisms. Specifically, 5-chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine is not stable at room temperature and it undergoes dimerization as shown in Scheme 1 (the resulting product is hereinafter referred to as "Dimer").

The dimers and related adducts are described in Application Ser. No. 60/751,166, as filed on Dec. 16, 2005, the disclosure of which is hereby incorporated by reference in its entirety. In particular, the dimers, adducts, methods for making and using same are incorporated by reference herein.

Scheme 1

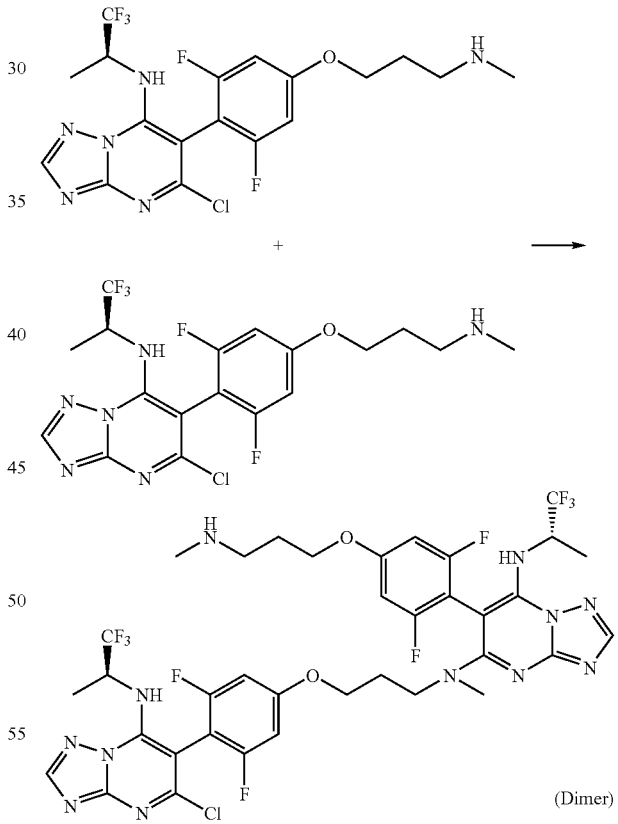

In addition, the hydrochloric acid salt of 5-chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine has been found to have good aqueous solubility, but the material is amorphous. Thus, there remains a need to identify a crystalline form of 5-chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine that is water soluble and has good stability under various storage conditions.

In accordance with the present invention, the 5-chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine salts, including the succinate salts (anhydrous and dihydrate), the fumarate salts (dihydrate), and the mandelate salt, are provided in crystalline forms, described further hereinbelow.

SUMMARY OF THE INVENTION

The present invention relates to crystalline forms of 5-chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine salts, including the succinate salts (anhydrous and dihydrate), the fumarate salts (dihydrate), and the mandelate salts; processes for the production thereof; pharmaceutical compositions thereof; and methods for inhibiting tumor growth therewith.

DETAILED DESCRIPTION OF THE INVENTION

The present invention provides crystalline forms of 5-chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine salts, including the succinate salts (anhydrous and dihydrate), the fumarate salts (dihydrate), and the mandelate salt. The invention also provides crystalline forms of such 5-chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine salts, which are substantially pure, i.e., more than about 90% pure.

The crystalline forms of the instant invention can be characterized using X-Ray Powder Diffraction (XRPD), Differential Scanning Calorimetry (DSC), and Thermogravimetric Analysis (TGA). It is to be understood that numerical values described and claimed herein are approximate. Variation within the values may be attributed to equipment calibration, equipment errors, purity of the materials, crystal size, and sample size, among other factors. In addition, variation may be possible while still obtaining the same result. For example, X-ray diffraction values are generally accurate to within ±0.2 degrees and intensities (including relative intensities) in an X-ray diffraction pattern may fluctuate depending upon measurement conditions employed. Similarly, DSC results are typically accurate to within about 2° C. Consequently, it is to be understood that the crystalline forms of the instant invention are not limited to the crystalline forms that provide characterization patterns (i.e., one or more of the XRPD, DSC and TGA) completely identical to the characterization patterns depicted in the accompanying Figures disclosed herein. Any crystalline forms that provide characterization patterns substantially the same as those described in the accompanying Figures fall within the scope of the present invention. The ability to ascertain substantially the same characterization patterns is within the purview of one of ordinary skill in the art.

Figure 1:
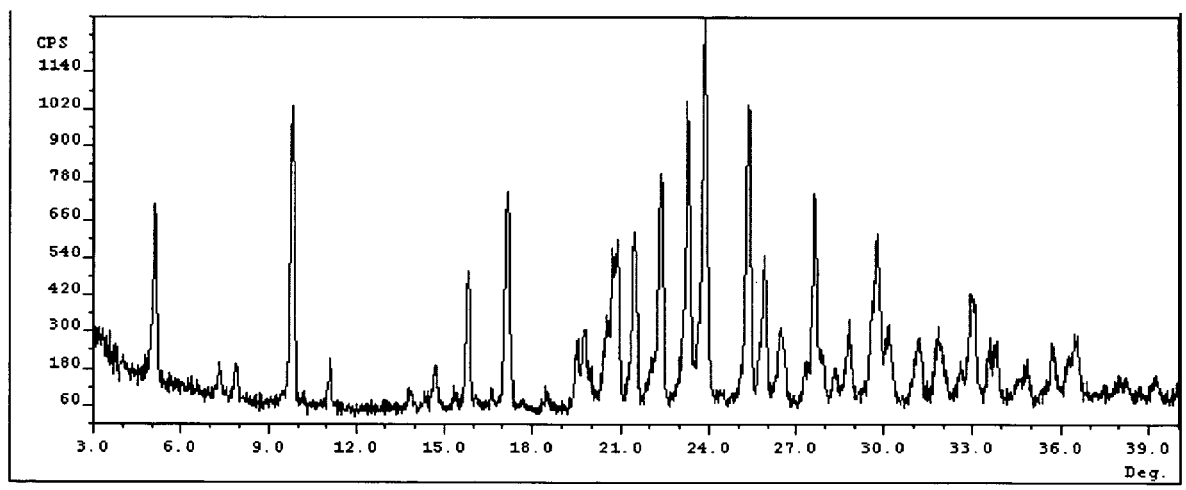
FIG. 1 is a powder x-ray diffraction pattern for 5-chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine succinate dihydrate.

In one aspect of the invention, there is provided a crystalline form of 5-chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine succinate dihydrate, which exhibits an XRPD pattern substantially the same as that depicted in FIG. 1, comprising one or more 2θ values selected from: 5.1±0.2, 9.8±0.2, 11.1±0.2, 15.8±0.2, 17.1±0.2, 21.5±0.2, 22.4±0.2, 23.3±0.2, 23.9±0.2, 25.3±0.2, 25.8±0.2, 27.6±0.2 and 29.8±0.2. The invention also provides a crystalline form of 5-chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine succinate dihydrate that exhibits an XRPD pattern having characteristic diffraction peaks expressed in degrees 2-theta, at approximately the values shown in Table 1 (Column 2) hereinbelow.

Figure 2:
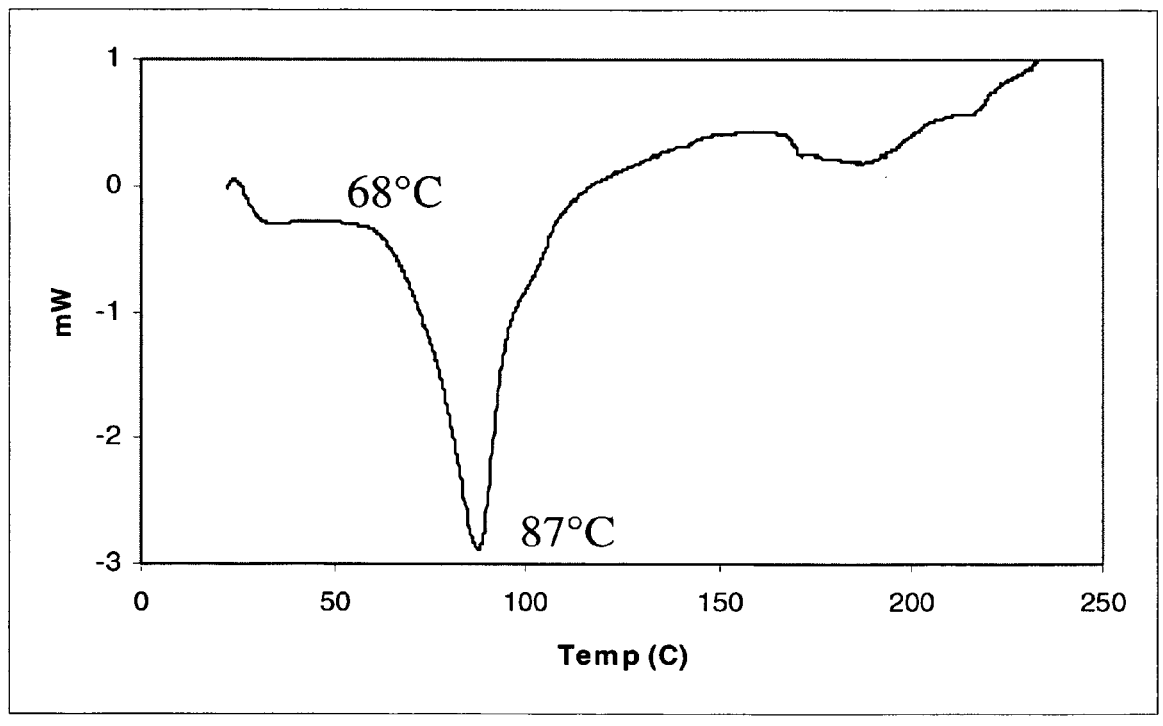
FIG. 2 is a DSC thermogram for 5-chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine succinate dihydrate.

In another aspect, the invention provides a crystalline form of 5-chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine succinate dihydrate, which exhibits a differential scanning calorimetry (DSC) thermogram having an endotherm onset at about 68° C. The invention also provides a crystalline form of 5-chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine succinate dihydrate that exhibits a DSC thermogram substantially the same as shown in FIG. 2.

Figure 3:
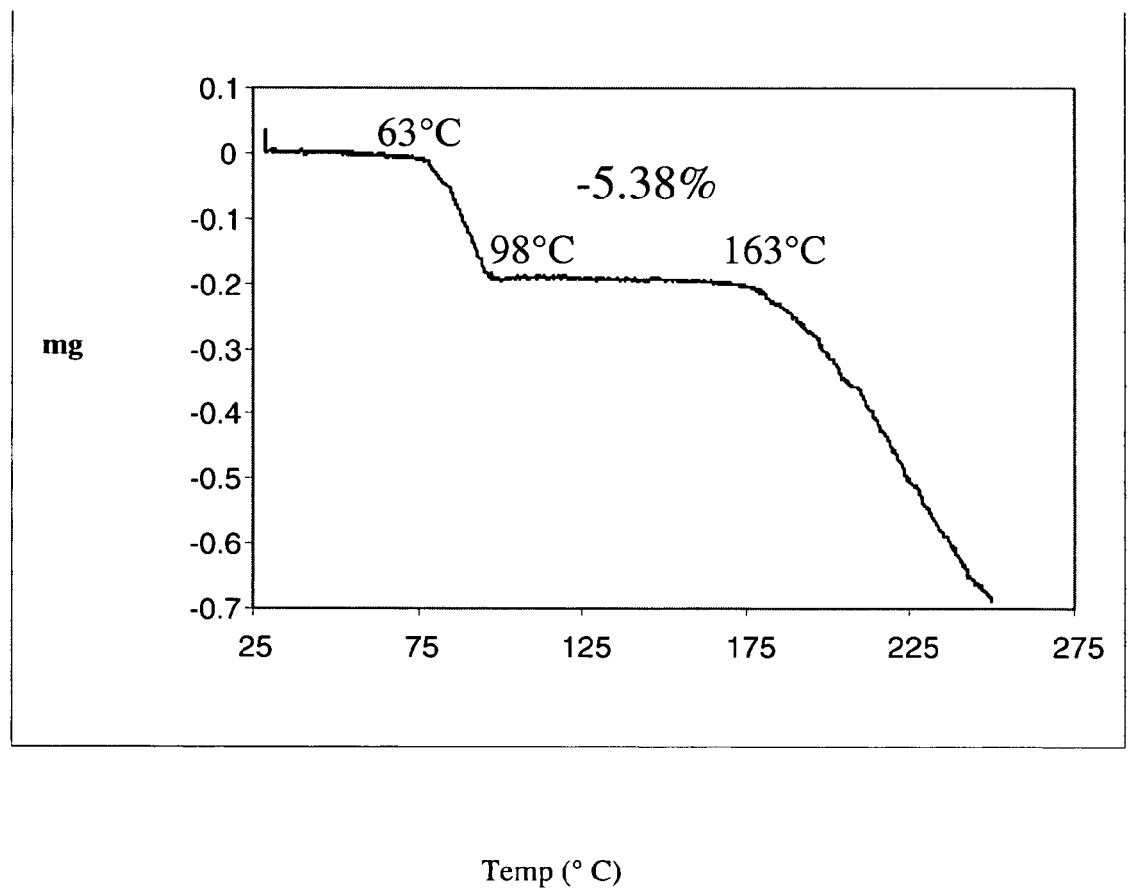
FIG. 3 is a TGA thermogram for 5-chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine succinate dihydrate.

In yet another aspect, the invention provides a crystalline form of 5-chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine succinate dihydrate, which exhibits a thermogravimetric analysis (TGA) thermogram having minimal weight loss for a dihydrate form, wherein about 5.4-6.0% weight loss was observed. The invention also provides a crystalline form of 5-chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine succinate dihydrate, which exhibits a TGA thermogram substantially the same as shown in FIG. 3.

Figure 4:
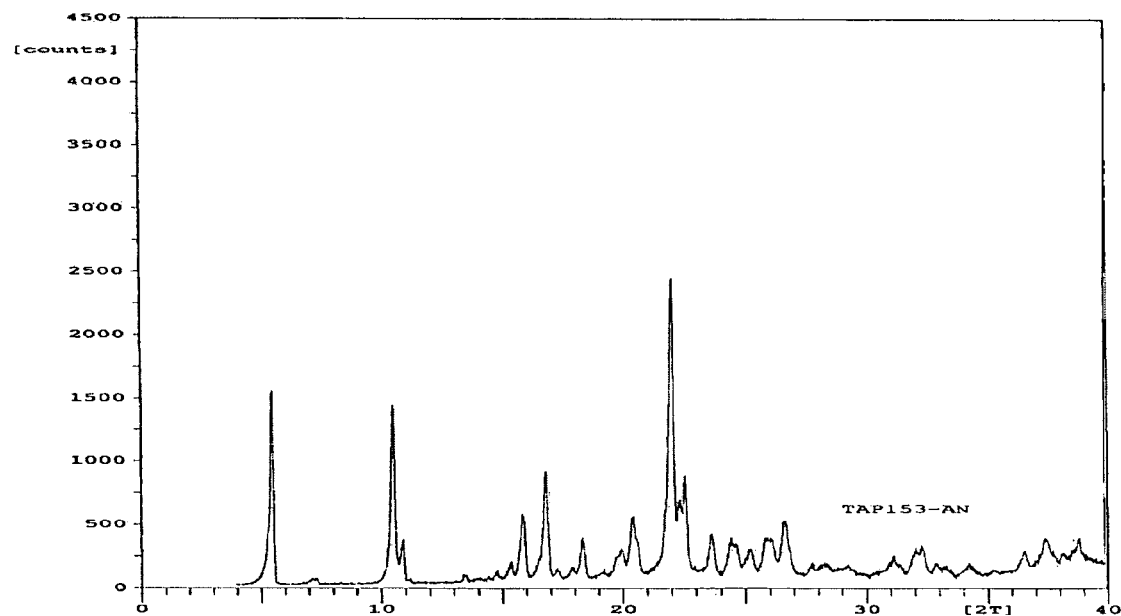
FIG. 4 is a powder x-ray diffraction pattern for 5-chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine succinate anhydrous.

In a further aspect, the invention provides a crystalline form of 5-chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine succinate anhydrous, which exhibits an XRPD pattern substantially the same as that depicted in FIG. 4, comprising one or more 2θ values selected from: 5.4±0.2, 10.4±0.2, 10.8±0.2, 15.6±0.2, 16.8±0.2, 18.2±0.2, 22.1±0.2, and 23.6±0.2. The invention also provides a crystalline form of 5-chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine succinate anhydrous that exhibits an XRPD pattern having characteristic diffraction peaks expressed in degrees 2-theta, at approximately the values shown in Table 1 (Column 1) below.

Figure 5:
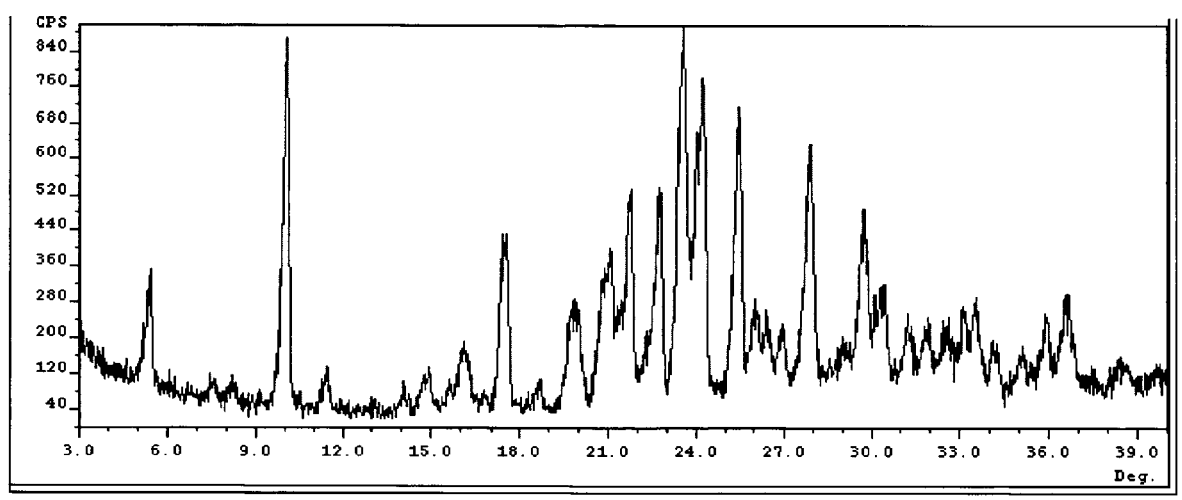
FIG. 5 is a powder x-ray diffraction pattern for 5-chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine furamate dihydrate.

In another aspect, the invention provides a crystalline form of 5-chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine furamate dihydrate, which exhibits an XRPD pattern substantially the same as that depicted in FIG. 5, comprising one or more 2θ values selected from: 5.4±0.2, 10.1±0.2, 17.4±0.2, 21.8±0.2, 22.8±0.2, 23.6±0.2, 24.2±0.2, 25.4±0.2, 27.9±0.2, and 29.7±0.2. The invention also provides a crystalline form of 5-chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine furamate dihydrate that exhibits an XRPD pattern having characteristic diffraction peaks expressed in degrees 2-theta, at approximately the values shown in Table 1 (Column 3) below.

Figure 6:
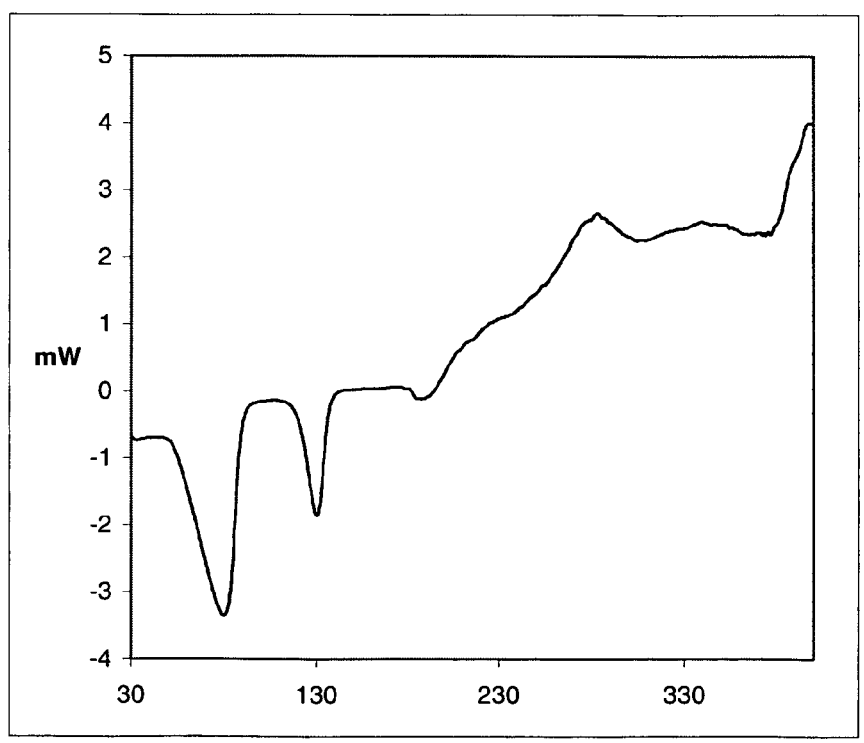
FIG. 6 is a DSC thermogram for 5-chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine furamate dihydrate.

In yet another aspect, the invention provides a crystalline form of 5-chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine fumarate dihydrate, which exhibits a differential scanning calorimetry (DSC) thermogram comprising two endotherm onset at 53° C. and 119° C. The invention also provides a crystalline form of 5-chloro-6-{2,6-difluoro-4-[3-(methylamino) propoxy]phenyl}-N-[(1S)-2,2,2-trifluoro-1-methylethyl][1,2,4]triazolo[1,5-a]pyrimidin-7-amine fumarate dihydrate that exhibits a DSC thermogram substantially the same as shown in FIG. 6.

Figure 7:
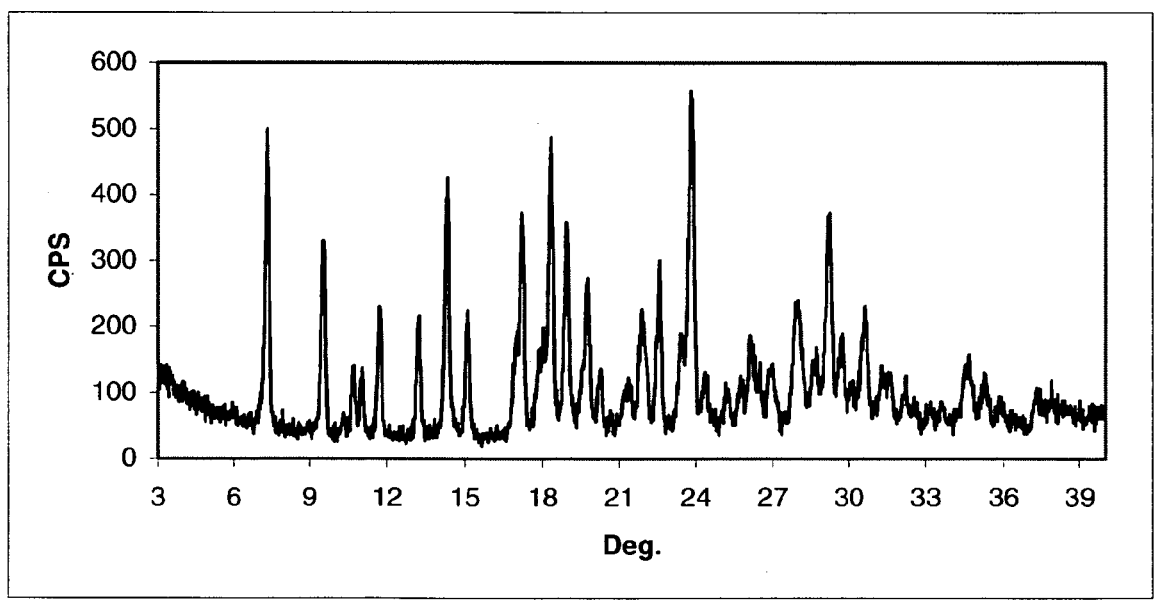
FIG. 7 is a powder x-ray diffraction pattern for 5-chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine mandelate.

In a further aspect, the invention provides a crystalline form of 5-chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine mandelate, which exhibits an XRPD pattern substantially the same as that depicted in FIG. 7, comprising one or more 2θ values selected from: 7.3±0.2, 9.6±0.2, 11.7±0.2, 13.2±0.2, 14.3±0.2, 15.1±0.2, 17.2±0.2, 18.3±0.2, 19.0±0.2, 19.8±0.2, 21.9±0.2, 22.6±0.2, 23.8±0.2, 28.0±0.2, and 29.2±0.2. The invention also provides a crystalline form of 5-chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine mandelate that exhibits an XRPD pattern having characteristic diffraction peaks expressed in degrees 2-theta, at approximately the values shown in Table 1 (Column 4) below.

TABLE 1

Peak positions of the succinate anhydrous salt (Column 1), succinate dihydrate salt (Column 2), Mandelate salt (Column 4), and fumarate dihydrate salt (Column 3)
2-Theta angle (degree)

| Column 1 Succinate Anhydrate | Column 2 Succinate Dihydrate | Column 3 Fumarate Dihydrate | Column 4 Mandelate |
|---|---|---|---|
| 5.4 | 5.1 | 5.4 | 7.3 |
| 10.4 | 9.8 | 10.1 | 9.6 |
| 10.8 | 11.1 | 17.4 | 11.7 |
| 15.6 | 15.8 | 21.8 | 13.2 |
| 16.8 | 17.1 | 22.8 | 14.3 |
| 18.2 | 21.5 | 23.6 | 15.1 |
| 22.1 | 22.4 | 24.2 | 17.2 |
| 23.6 | 23.3 | 25.4 | 18.3 |
| | 23.9 | 27.9 | 19.0 |
| | 25.3 | 29.7 | 19.8 |
| | 25.8 | | 21.9 |
| | 27.6 | | 22.6 |
| | 29.8 | | 23.8 |
| | | | 28.0 |
| | | | 29.2 |

Figure 8:
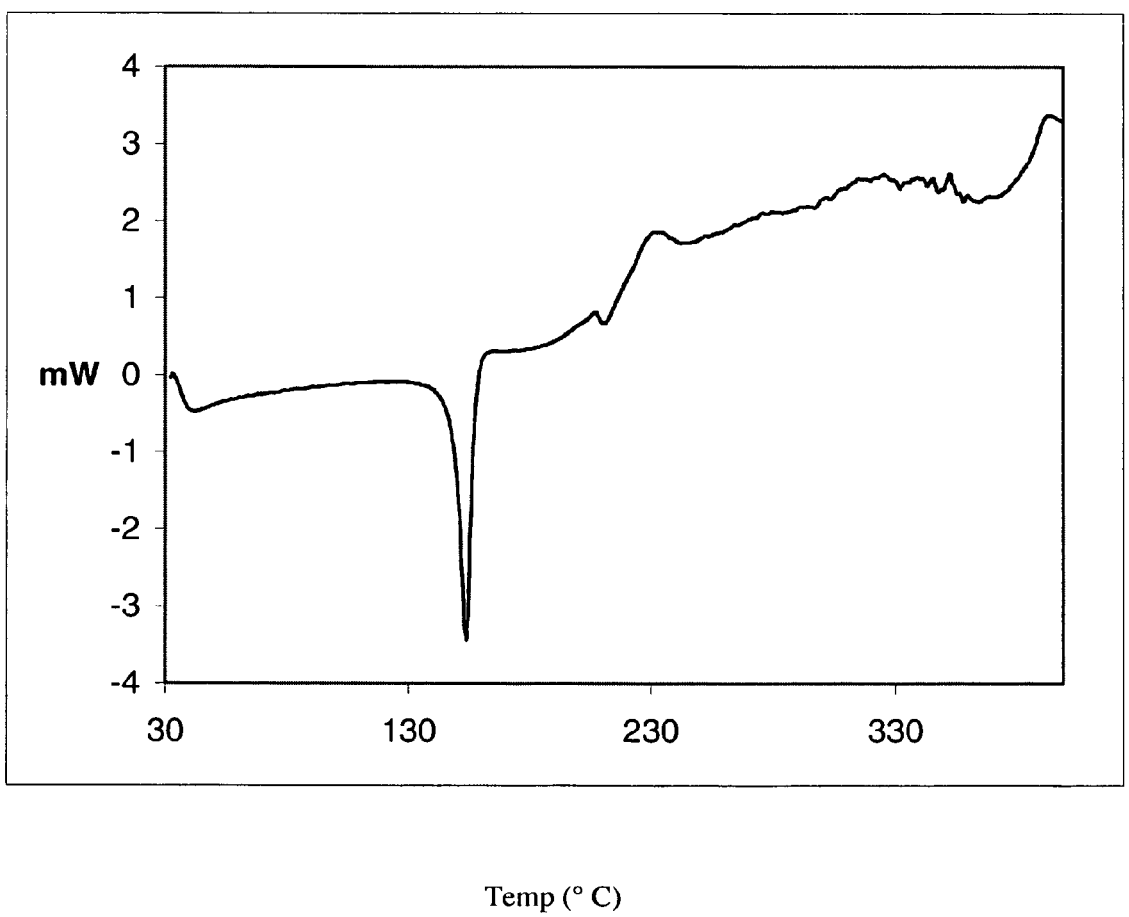
FIG. 8 is a DSC thermogram for 5-chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine mandelate.

In yet another aspect, the invention provides a crystalline form of 5-chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine mandelate, which exhibits a differential scanning calorimetry (DSC) thermogram comprising an endotherm onset at about 146° C. The invention also provides a crystalline form of 5-chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine mandelate that exhibits a DSC thermogram substantially the same as shown in FIG. 8.

It should be understood that this invention encompasses all crystalline and hydrated forms of 5-chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine and their pharmaceutic acceptable salts. The term "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The term "pharmaceutically acceptable salt" as used herein refers to a salt of an acid and a basic nitrogen atom of a compound of the present invention. The term "pharmaceutically acceptable salt" also includes hydrates of a compound of the present invention, or hydrates of a pharmaceutically acceptable salt of a compound of the present invention. Exemplary salts include, but are not limited to, sulfate, citrate, acetate, oxalate, chloride, hydrochloride, bromide, hydrobromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, camphorsulfonate, napthalenesulfonate, propionate, succinate, fumarate, maleate, malonate, mandelate, malate, phthalate, pamoate, hydrates, or hydrates of the above mentioned salts. A further salt is the trifluoroacetic acid salt (TFA). In particular, the fumarate, succinate, and mandelate salts are preferred.

In a further aspect, the invention provides a process for preparing a crystalline form of 5-chloro-6-{2,6-difluoro-4-[3-(methylamino)propoxy]phenyl}-N-[(1S)-2,2,2-trifluoro- 1-methylethyl][1,2,4]triazolo[1,5-a]pyrimidin-7-amine succinate dihydrate, which process comprises crystallizing a mixture of 5-chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine and succinic acid from water.

In yet another aspect, the invention provides a process for preparing a crystalline form of 5-chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine succinate anhydrous, which process comprises crystallizing a mixture of 5-chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine and succinic acid from water followed by drying.

In yet another aspect, the invention provides a process for preparing a crystalline form of 5-chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine fumarate dihydrate, which process comprises crystallizing a mixture of 5-chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine and fumaric acid from water.

In yet another aspect, the invention provides a process for preparing a crystalline form of 5-chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine mandelate, which process comprises crystallizing a mixture of 5-chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine and mandelic acid from water.

Pharmaceutically acceptable salts of the compound of the invention are contemplated in the present invention. As a representative example of pharmaceutically acceptable salt formation, the hydrochloride salt of 5-chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine, is neutralized with aqueous alkali metal hydroxide or aqueous alkali metal carbonate, and further reacted with a suitable pharmaceutically acceptable salt forming acid described hereinabove in a suitable solvent. Suitable solvents which may be used include: water, acid, methanol, ethanol, isopropanol or combination thereof and the like. A preferred solvent is water.

Preferably, pharmaceutically acceptable salts may form by heating 5-chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine and a suitable pharmaceutically acceptable acid in a suitable solvent, at about 30-100° C., preferably at about 65-75° C., until a clear solution forms. Upon cooling the compound may be collected and dried.

Using the conditions described hereinabove, the crystalline forms of 5-chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine succinate salts (anhydrous and hydrate), 5-chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine fumarate salts (anhydrous and hydrate), and 5-chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine mandelate salt may be produced. In particular, dihydrates may be formed by optional further contact with water or an atmosphere of water at about 80-100% relative humidity at room temperature.

In a further aspect, the invention provides a pharmaceutical composition comprising a crystalline form of 5-chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine succinate dihydrate and at least one pharmaceutically acceptable carrier or excipient.

In another aspect, the invention provides a pharmaceutical composition comprising a crystalline form of 5-chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine succinate anhydrous and at least one pharmaceutically acceptable carrier or excipient.

In yet another aspect, the invention provides a pharmaceutical composition comprising a crystalline form of 5-chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine fumarate dihydrate and at least one pharmaceutically acceptable carrier or excipient.

In yet another aspect, the invention provides a pharmaceutical composition comprising a crystalline form of 5-chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine fumarate anhydrous and at least one pharmaceutically acceptable carrier or excipient.

In yet another aspect, the invention provides a pharmaceutical composition comprising a crystalline form of 5-chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine mandelate and at least one pharmaceutically acceptable carrier or excipient.

The phrase "pharmaceutically acceptable carrier or excipients" as used herein means a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body. Each carrier must be "acceptable" in the sense of being compatible with the other ingredients of the formulation. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline, (18) Ringer's solution, (19) ethyl alcohol; (20) phosphate buffer solutions; and (21) other non-toxic compatible substances employed in pharmaceutical formulations.

Pharmaceutically acceptable carriers or excipients include, without limitation, polyether glycols, saturated or unsaturated polyglycolized glyceridea, solid amphiphilic surfactants, surfactants other than said solid amphiphilic surfactants, alcohols other than a polyether glycols, fatty acid ester derivatives of polyhydric alcohols, vegetable oils, mineral oils, and an effective amount of a pharmaceutically acceptable acid for enhancing the stability of the drug. It should be understood that the crystalline forms of the present invention, e.g., the crystalline forms of the succinate salts (anhydrous and dihydrate), the fumarate salts (anhydrous and dihydrate), and the mandelate salt, may in some cases change to other form or forms (e.g., amorphous), or solublize, upon mixing with at least one pharmaceutically acceptable carrier or excipient.

Pharmaceutically acceptable carriers or excipients suitable for IV injection include, for example, water, at least one bulking agent and an effective amount of at least one pharmaceutically acceptable acid for enhancing the stability of the drug. Suitable bulking agents include carbohydrates such as mannitol, dextrose, dextran, or sucrose. Optionally, additional bulking agents such as polyvinylpyrrolidone, starch, lactose, trehalose or hydroxyethylstarch or glycerol may be used. Combinations of the above bulking agents can also be used.

In a further aspect, the invention provides a method of treating or inhibiting the growth of cancerous tumor cells and associated diseases in a mammal in need thereof, which method comprises administering to the mammal an effective amount of a crystalline form of 5-chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine succinate dihydrate, or succinate anhydrous, or fumarate dihydrate, or mandelate, or a pharmaceutical composition containing such crystalline form of 5-chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine succinate dihydrate, or succinate anhydrous, or fumarate dihydrate, or mandelate.

In another aspect, the invention provides a method of promoting tubulin polymerization in a tubulin containing system which comprises contacting said tubulin containing system with an effective amount of a crystalline form of 5-chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine succinate dihydrate, or succinate anhydrous, or fumarate dihydrate, or or mandelate, or a pharmaceutical composition containing such crystalline form of 5-chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine succinate dihydrate, or succinate anhydrous, or fumarate dihydrate, or mandelate.

In yet another aspect, the invention provides a method of stabilizing microtubules in a tubulin containing system which comprises contacting said tubulin containing system with an effective amount of a crystalline form of 5-chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine succinate dihydrate, or succinate anhydrous, or fumarate dihydrate, or mandelate, or a pharmaceutical composition containing such crystalline form of 5-chloro-6-{2,6-difluoro-4-[3-(methylamino) propoxy]phenyl}-N-[(1S)-2,2,2-trifluoro-1-methylethyl][1,2,4]triazolo[1,5-a]pyrimidin-7-amine succinate dihydrate, or succinate anhydrous, or fumarate dihydrate, or mandelate.

In yet another aspect, the invention provides a method for the treatment or prevention of tumors that express multiple drug resistance (MDR) or are resistant because of MDR in a mammal in need thereof, which method comprises administering to said mammal an effective amount of a crystalline form of 5-chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine succinate dihydrate, or succinate anhydrous, or fumarate dihydrate, or mandelate, or a pharmaceutical composition containing such crystalline form of 5-chloro-6-{2,6-difluoro-4-[3-(methylamino) propoxy]phenyl}-N-[(1S)-2,2,2-trifluoro-1-methylethyl][1,2,4]triazolo[1,5-a]pyrimidin-7-amine succinate dihydrate, or succinate anhydrous, or fumarate dihydrate, or mandelate.

Based on the results of standard pharmacological test procedures described herein, the compounds of this invention are useful as agents for treating, inhibiting or controlling the growth of cancerous tumor cells and associated diseases in a mammal in need thereof. The compounds of the invention are useful as agents for treating, inhibiting or controlling the growth of cancerous tumor cells and associated diseases in a mammal in need thereof by interacting with tubulin and microtubules and promoting microtubule polymerization. The compounds of the invention are also useful for the treatment or prevention of cancerous tumors that express multiple drug resistance (MDR) or are resistant because of MDR.

In particular, contacting a tubulin containing system with an effective amount of a compound of the present invention results in the promotion of microtubule polymerization and further stabilizes microtubules. By promoting microtubule polymerization and stabilizing microtubules, said compounds of the present invention are useful as agents for treating, inhibiting or controlling the growth of cancerous tumor cells and associated diseases. The tubulin containing system may be in a tumor cell, thereby inhibiting neoplastic disease by administering an effective amount of a compound described in the present invention. Mammals may be treated and in particular, humans. Further, said tubulin containing system may be in a patient.

In the case of cancer treatment, it is believed that many neoplasias such as leukemia, lung cancer, colon cancer, thyroid cancer, ovarian cancer, renal cancer, prostate cancer and breast cancers may be treated by effectively administering effective amounts of the compounds of the present invention. Additionally, compounds of the present invention are useful for the treatment or prevention of cancerous tumors that express multiple drug resistance (MDR) or are resistant because of MDR. As used herein, cancer refers to all types of cancers, or neoplasms or benign or malignant tumors. Preferred cancers for treatment using methods provided herein include carcinoma, sarcoma, lymphoma, or leukemia. By carcinoma is meant a benign or malignant epithelial tumor and includes, but is not limited to, breast carcinoma, prostate carcinoma, non-small lung carcinoma, colon carcinoma, melanoma carcinoma, ovarian carcinoma, or renal carcinoma. A preferred host is a human.

The effective dosage of active ingredient employed may vary depending on the particular compound employed, the mode of administration and severity of the condition being treated. However, in general satisfactory results are obtained when the compounds of the invention are administered in amounts ranging from about 0.10 to about 50 mg/kg of body weight per day. A preferred regimen for optimum results would be from about 1 mg to about 15 mg/kg of animal weight per day and such dosage units are employed so that a total of from about 4.5 mg/m$^2$ of the active compound for a subject of about 70 kg of body weight are administered in a 24 hour period. The dosage regimen for treating mammals may be adjusted to provide the optimum therapeutic response. For example, several divided doses may be administered daily or the dose may be proportionally reduced as indicated by the exigencies of the therapeutic situation. A decidedly practical advantage is that these active compounds may be administered in any convenient manner such as by the oral, intravenous, intramuscular or subcutaneous routes. It is understood that the actual effective amount will be established by dose/response assays using methods standard in the art (Johnson et al., *Diabetes*. 42:1179, (1993)). Thus, as is known to those in the art, the effective amount will depend on bioavailability, bioactivity, and biodegradability of the compound.

The active compounds of the invention may preferably be orally administered, for example, with an inert diluent or with an assimilable edible carrier, or they may be enclosed in hard or soft shell gelatin capsules, or they may be compressed into tablets or they may be incorporated directly with the food of the diet. For oral therapeutic administration, these active compounds may be incorporated with excipients and used in the form of ingestible tablets, buccal tablets, troches, capsules, elixirs, suspensions, syrups, wafers and the like. Such compositions and preparations should contain at least 0.1% of active compound. The percentage of the compositions and preparations may, of course, be varied and may conveniently be between about 2% to about 60% of the weight of the unit. The amount of active compound in such therapeutically useful compositions is such that a suitable dosage will be obtained. Preferred compositions or preparations according to the present invention are prepared so that an oral dosage unit form contains between 10 and 1000 mg of active compound.

The tablets, troches, pills, capsules and the like may also contain one or more of the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose, or saccharin may be added or a flavoring agent such as peppermint, oil of wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills or capsules may be coated with shellac, sugar or both. A syrup or elixir may contain the active compound, sucrose, as a sweetening agent, methyl and propylparabens as preservatives, a dye and flavoring such as cherry or orange flavor. Of course, any material used in preparing any dosage unit form should be pharmaceutically pure and substantially non-toxic in the amounts used. In addition, these active compounds may be incorporated into sustained-release preparations and formulations.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid polyethylene glycols, or mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be prepared against the contaminating action of microorganisms such as bacteria and fungi. The carrier can be a solvent or dispersion medium containing, for example, water, ethanol, polyol (e.g., glycerol, propylene glycol and liquid poly-ethylene glycol), suitable mixtures thereof, and vegetable oils.

Intravenous administration is a preferred manner of administration of compounds of the invention. For intravenous administration examples of non-limiting suitable carriers include physiological saline, bacteriostatic water, Cremophor ELTM (BASF, Parsippany, N.J.) or phosphate buffered saline (PBS). The composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, and sodium chloride in the composition. Prolonged absorption of the injectable compositions can be brought about by including in the composition an agent which delays absorption, for example, aluminum monostearate and gelatin.

As used in accordance with this invention, the term providing an effective amount of a compound means either directly administering such compound, or administering a prodrug, derivative, or analog which will form an effective amount of the compound within the body. The phrase "effective amount" as used herein means that amount of one or more agent, material, or composition comprising one or more agents of the present invention that is effective for producing some desired effect in an animal. It is recognized that when an agent is being used to achieve a therapeutic effect, the actual dose which comprises the "effective amount" will vary depending on a number of conditions including the particular condition being treated, the severity of the disease, the size and health of the patient, the route of administration, etc. A skilled medical practitioner can readily determine the appropriate dose using methods well known in the medical arts.

In certain embodiments, the active compounds of the invention are administered in combination with additional agents. For example, the administration of the compounds may be part of a therapeutic regimen to treat a particular condition or part of a combinatorial therapy with other agents. Combination therapy refers to any form of administration in combination of two or more different therapeutic compounds such that the second compound is administered while the previously administered therapeutic compound is still effective in the body (e.g., the two compounds are simultaneously effective in the patient, which may include synergistic effects of the two compounds). For example, the different therapeutic compounds can be administered either in the same formulation or in a separate formulation, either concomitantly or sequentially. Thus, an individual who receives such treatment can have a combined (conjoint) effect of different therapeutic compounds.

In addition to the above utilities, some of the compounds of this invention are useful for the preparation of other compounds of this invention.

Examples of this invention are evaluated in several standard pharmacological test procedures that showed that the compounds of this invention possess significant activity as promoters of microtubule polymerization and are antineoplastic agents. Based on the activity shown in the standard pharmacological test procedures, the compounds of this invention are therefore useful as anticancer agents. Associated cancers are selected from the group consisting of breast, colon, lung, prostate, melanoma, epidermal, leukemia, kidney, bladder, mouth, larynx, esophagus, stomach, ovary, pancreas, liver, skin and brain. In particular, the compounds of this invention possess an effect similar to Paclitaxel. The test procedures used and results obtained are shown below.

The following examples are further illustrative of the present invention. The present invention is not limited to the percentages, components and techniques described herein.

EXPERIMENTAL

Powder X-Ray Diffraction (PXRD)

A Scintag X-ray diffractometer is used to collect the diffraction data. The diffraction intensity is collected at a scan rate of 2.4 degree per minute between 2-theta angle of 3° and 40°. Table 1 lists the peak positions or 2-theta angles of the corresponding PXRD patterns.

Powder XRD measurement indicates that the anhydrous and hydrated 5-chloro-6-{2,6-difluoro-4-[3-(methylamino) propoxy]phenyl}-N-[(1S)-2,2,2-trifluoro-1-methylethyl][1,2,4]triazolo[1,5-a]pyrimidin-7-amine succinate salt (Example 2c) and the anhydrous and hydrated 5-chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine fumarate salt (Example 2b) obtained are crystalline and are different crystalline structures. A Scintag X-ray diffractometer is used to collect the diffraction data. The diffraction intensity is collected at a scan rate of 2.4 degree per minute between 2-theta angle of 3° and 40°.

Differential Scanning Calorimetry (DSC)

Differential scanning calorimetry (DSC) experiments were performed in a Shimadzu DSC-50. The sample (about 2 mg) was weighed in an aluminum pan and recorded accurately recorded to a hundredth of a milligram, and transferred to the DSC. The instrument was purged with nitrogen gas at 20 mL/min. Data were collected between room temperature and 350° C. at 10° C./min heating rate. The plot was made with the endothermic peaks pointing down.

Thermogravimetric Analysis (TGA)

Thermal gravimetric analysis (TGA) experiments were performed in a Shimadzu TGA-50. The sample (about 2-5 mg) was placed in a platinum pan previously tared. The weight of the sample was measured accurately and recorded to a thousand of a milligram by the instrument. The furnace was purged with nitrogen gas at 30 mL/min. Data were collected between room temperature and 350° C. at 10° C./min heating rate.

METHODS OF PREPARATION

EXAMPLE 1

5-Chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine

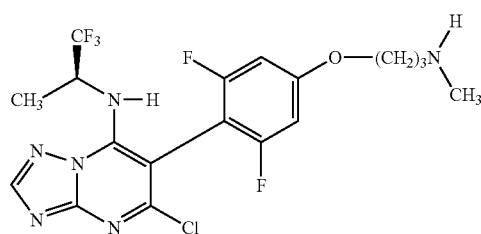

To sodium hydride (60% in mineral oil, 2.3 g, 57.6 mmol) in 20 mL of dimethylsulfoxide at room temperature is added a solution of 3-(methylamino)propan-1-ol (5.14 g, 57.6 mmol) in 10 mL of dimethylsulfoxide. The solution is stirred at room temperature for 1 h, and 5-chloro-6-(2,4,6-trifluorophenyl)-N-[(1S)-2,2,2-trifluoro-1-methylethyl][1,2,4]triazolo[1,5-a]pyrimidin-7-amine (5.7 g, 14.4 mmol) is added. The mixture is heated at 60° C. for 3 h, and cooled to room temperature. The reaction mixture is diluted with ethyl acetate, and washed with water and saturated sodium chloride. The organic layer is dried over magnesium sulfate, and concentrated to a residue. The residue is triturated with small amount of acetone, then hexanes, and chromatographed over silica gel, eluting with a gradient of 100% ethyl acetate to 100% methyl alcohol. Concentration provides 5-chloro-6-{2,6-difluoro-4-[3-(methylamino) propoxy]phenyl}-N-[(1S)-2,2,2-trifluoro-1-methylethyl][1,2,4]triazolo[1,5-a]pyrimidin-7-amine as a white solid (2.7 g). MS: m/z 465.1 (M+H).

EXAMPLE 2a

5-Chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine hydrogen chloride The product of Example 1 is dissolved in 10% methyl alcohol in methylene chloride (150 mL) and filtered. To the filtrate is bubbled hydrogen chloride gas. Concentration provides 5-chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine hydrogen chloride salt as a light yellow solid (2.92 g).

EXAMPLE 2b

5-Chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine fumarate salt To a slurry of 5-chloro-6-{2,6-difluoro-4-[3-(methylamino)propoxy]phenyl}-N-[(1S)-2,2,2-trifluoro-1-[1,2,4]triazolo[1,5-a]pyrimidin-7-amine hydrochloride (7.50 g, 15.0 mmol) and water (100 mL) is added sodium hydroxide solution (10 N, 2.0 mL, 20 mmol) dropwise. Then, fumaric acid (3.48 g, 30 mmol) is added. The mixture is stirred for about 15-20 min and then heated to about 65-75° C. and stirred until all of the solid dissolves. The solution is filtered and the filtrate is cooled to about 0-5° C. over about 1 h. The mixture is stirred for 1 h and then filtered and the collected solid washed with cold water and isopropanol. The solid is dried under vacuum at about 60° C./10 mmHg for about 20 h to give a white solid (6.54 g, 75%) in anhydrous form. A portion of the compound is placed in a drying dish at 80-100% relative humidity (RH) and room temperature for about 24 h. The compound absorbed 5.8% water forming a dihydrate which is stable at room temperature and at 5-100% relative humidity (RH).

$^1$H NMR (CDCl$_3$): δ 8.43 (s, 1H), 6.86 (d, 2H, J=10.2 Hz), 6.51 (s, 2H), 5.84 (m, 1H), 4.15 (t, 2H, J=7.9 Hz), 3.04 (t, 2H, J=7.2 Hz), 2.57 (s, 3H), 2.08 (m, 2H), 1.33 (d, J=6.7, 3H).

This compound absorbs two mole waters at 5%-100% RH to become its dihydrate. 5-Chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine fumarate salt dihydrate.

EXAMPLE 2c

5-Chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine succinate salt A mixture of 5-chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine (9.00 g, 19.4 mmol) and succinic acid (2.75 g, 23.3 mmol) in water (90 mL) is stirred for about 15-20 min and then heated to about 65-75° C. The solution is filtered and the filtrate is cooled to about 0-5° C. over about 1 h. The mixture is stirred for about 1 h and then filtered and the collected solid washed with cold water (2×9 mL) and cold isopropanol (9 mL). The solid is dried under vacuum at about 40° C./10 mmHg for about 20 h to give a white solid in anhydrous form (6.6 g, 73%). A portion of the compound is placed in a drying dish at 80-100% relative humidity (RH) and room temperature for about 24 h. The compound absorbed 5.8% water forming a dihydrate which is stable at room temperature and at 5-100% relative humidity (RH). $^1$H NMR (CDCl$_3$): δ 10.2 (bs, 1H), 8.26 (s, 1H), 6.80 (d, 2H, J=10.5 Hz), 5.79 (m, 1H), 4.13 (t, 2H, J=6.3 Hz), 3.03 (t, 2H, J=7.2 Hz), 2.57 (s, 3H), 2.35 (s, 4H), 2.07 (m, 2H), 1.27 (d, J=6.0, 3H). This compound absorbs two mole waters at 5%-100% RH to become its dihydrate, 5-chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine succinate salt dihydrate.

We claim:

1. A crystalline form of 5-chloro-6-{2,6-difluoro-4-[3-(methylamino) propoxy]phenyl}-N-[(1S)-2,2,2-trifluoro-1-methylethyl][1,2,4]triazolo[1,5-a]pyrimidin-7-amine succinate dihydrate, which exhibits a powder X-ray diffraction pattern comprising 2θ values selected from: 5.1±0.2, 9.8±0.2, 11.1±0.2, 15.8±0.2, 17.1±0.2, 21.5±0.2, 22.4±0.2, 23.3±0.2, 23.9±0.2, 25.3±0.2, 25.8±0.2, 27.6±0.2 and 29.8±0.2.

2. A crystalline form of 5-chloro-6-{2,6-difluoro-4-[3-(methylamino) propoxy]phenyl}-N-[(1S)-2,2,2-trifluoro-1-methylethyl][1,2,4]triazolo[1,5-a]pyrimidin-7-amine succinate dihydrate, which exhibits a DSC thermogram comprising an endotherm onset at about 68° C.

3. A crystalline form of 5-chloro-6-{2,6-difluoro-4-[3-(methylamino) propoxy]phenyl}-N-[(1S)-2,2,2-trifluoro-1-methylethyl][1,2,4]triazol[1,5-a]pyrimidin-7-amine succinate dihydrate, which exhibits a TGA thermogram having about 5.4-6.0% weight loss.

4. A process for preparing a crystalline form of 5-chloro-6-{2,6-difluoro-4-[3-methylamino)propoxy]phenyl}-N-[(1S)-2,2,2-trifluoro-1-methylethyl][1,2,4]triazolo[1,5-a]pyrimidin-7-amine succinate dihydrate, which process comprises crystallizing a mixture of 5-chloro-6-{2,6-difluoro-4-[3-(methylamino) propoxy]phenyl}-N-[(1S)-2,2,2-trifluoro-1-methylethyl][1,2,4]triazolo[1,5-a]pyrimidin-7-amine and succinic acid from water.

5. A crystalline form of 5-chloro-6-{2,6-difluoro-4-[3-(methylamino) propoxy]phenyl}-N-[(1S)-2,2,2-trifluoro-1-methylethyl][1,2,4]triazolo[1,5-a]pyrimidin-7-amine succinate anhydrous, which exhibits a powder X-ray diffraction pattern comprising 2θ values selected from: 5.4±0.2, 10.4±0.2, 10.8±0.2, 15.6±0.2, 16.8±0.2, 18.2±0.2, 22.1±0.2, and 23.6±0.2.

6. A crystalline form of 5-chloro-6-{2,6-difluoro-4-[3-(methylamino) propoxy]phenyl}-N-[(1S)-2,2,2-trifluoro-1-methylethyl][1,2,4]triazolo[1,5-a]pyrimidin-7-amine fumarate dihydrate, which exhibits a powder X-ray diffraction pattern comprising 2θ values selected from: 5.4±0.2, 10.1±0.2, 17.4±0.2, 21.8±0.2, 22.8±0.2, 23.6±0.2, 24.2±0.2, 25.4±0.2, 27.9±0.2, and 29.7±0.2.

7. A crystalline form of 5-chloro-6-{2,6-difluoro-4-[3-(methylamino) propoxy]phenyl}-N-[(1S)-2,2,2-trifluoro-1-methylethyl][1,2,4]triazolo1,5-a]pyrimidin-7-amine fumarate dihydrate, which exhibits a DSC thermogram comprising two endotherm onsets at about 53° C. and about 119° C.

8. A crystalline form of 5-chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine mandelate.

9. The crystalline form of claim 8, which exhibits a powder X-ray diffraction pattern comprising 2θ values selected from: 7.3±0.2, 9.6±0.2, 11.7±0.2, 13.2±0.2, 14.3±0.2, 15.1±0.2, 17.2±0.2, 18.3±0,2, 19.0±0.2, 19.8±0.2, 21.9±0.2, 22.6±0.2, 23.8±0.2, 28.0±0.2, and 29.2±0.2.

10. The crystalline form of claim 8, which exhibits a DSC thermogram comprising an endotherm onset at about 146° C.

11. A process for preparing a crystalline form of 5-chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine succinate anhydrous, which process comprises crystallizing a mixture of 5-chloro-6-{2,6-difluoro-4-[3-(methylamino) propoxy]phenyl}-N-[(1S)-2,2,2-trifluoro-1-methylethyl][1,2,4]triazolo[1,5-a]pyrimidin-7-amine and succinic acid from water followed by drying.

12. A process for preparing a crystalline form of 5-chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine fumarate dihydrate, which process comprises crystallizing a mixture of 5-chloro-6-{2,6-difluoro-4-[3-(methylamino) propoxy]phenyl}-N-[(1S)-2,2,2-trifluoro-1-methylethyl][1,2,4]triazolo[1,5-a]pyrimidin-7-amine and fumaric acid from water.

13. A process for preparing the crystalline form of claim 8, which process comprises crystallizing a mixture of 5-chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine and mandelic acid from water.

14. A process for preparing a crystalline form of 5-chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine succinate dihydrate, which process comprises:

(a) crystallizing a mixture of 5-chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine and succinic acid from water to provide a solid in hydrate form;

(b) drying the solid in hydrate form to provide a solid in anhydrous form; and (c) allowing the solid in anhydrous form to reabsorb water to provide the crystalline form of 5-chloro-6-{2,6-difluoro-4-[3-(methylamino)propoxyl]phenyl}-N-[(1S)-2,2,2-trifluoro-1-methylethyl][1,2,4]triazolo[1,5-a]pyrimidin-7-amine succinate dihydrate.

15. A process for preparing a crystalline form of 5-chloro-6-{2,6-difluoro-4-[3-(methylamino)propoxyl]phenyl}-N-[(1S)-2,2,2-trifluoro-1-methylethyl][1,2,4]triazolo[1,5-a]pyrimidin-7-amine fumarate dihydrate, which process comprises:

(a) crystallizing a mixture of 5-chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine and fumaric acid from water to provide a solid in hydrate form;

(b) drying the solid in hydrate form to provide a solid in anhydrous form; and
(c) allowing the solid in anhydrous form to reabsorb water to provide the crystalline form of 5-chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine fumarate dihydrate.

* * * * *